United States Patent [19]

Perten

[11] Patent Number: 5,682,324
[45] Date of Patent: Oct. 28, 1997

[54] METHOD AND ARRANGEMENT FOR DETERMINING THE ABILITY OF WHEATFLOUR TO BIND WATER

[76] Inventor: Jan Perten, Friggavagon 4, S-182-63 Djursholm, Sweden

[21] Appl. No.: 624,480

[22] PCT Filed: Oct. 4, 1994

[86] PCT No.: PCT/SE94/00924

§ 371 Date: Apr. 4, 1996

§ 102(e) Date: Apr. 4, 1996

[87] PCT Pub. No.: WO95/10042

PCT Pub. Date: Apr. 13, 1995

[30] Foreign Application Priority Data

Oct. 4, 1993 [SE] Sweden ................................. 9303235
Jun. 29, 1994 [SE] Sweden ................................. 9402301

[51] Int. Cl.$^6$ ................................................ G01N 33/10
[52] U.S. Cl. ............................ 364/502; 73/169; 426/231
[58] Field of Search ............................. 364/502, 496, 364/550, 148, 551.01, 709.03; 73/169; 426/231, 19, 549, 506

[56] References Cited

PUBLICATIONS

Stear, Chapter 1.4 "Water–Binding Capacity of Dough Components and Dough Consistency Control" Handbook of Breadmaking Technology 1990 pp. 21–26.

Derwent's abstract No. 85-295412/47, Week 8547, Abstract of SU, 1157450 (Romanov V G), May 23, 1985.

Patent Abstracts of Japan, vol. 11, No. 91, P-558 abstract of JP, A, 61-243360 (Iseki & Co Ltd), Oct. 29, 1986.

Primary Examiner—James P. Trammell
Assistant Examiner—M. Kemper
Attorney, Agent, or Firm—Jacobson, Price, Holman & Stern, PLLC

[57] ABSTRACT

The invention relates to a method and apparatus for test determining the optimal water-binding ability of wheat flour in order to bake bread with a desired baking result. A predetermined quantity of wheat flour is mixed with water and prepared by working the flour and water together over a given period of time. The starch content of the flour is washed out so as to obtain the gluten content of the flour and therewith a so-called wet gluten piece. This procedure is repeated at least twice at mutually different preparation times but at mutually equal temperatures. The wet gluten piece obtained with each test is first weighed with its water content. The piece is then dried and weighed again. The weights obtained are marked in a coordinate system or are alternatively fed into a computer and form the basis on which the water-binding ability of the gluten of the wheat flour can be indicated at a relevant working time. In order to obtain optimal or desired baking results for a particular wheat flour, the wheat is defined with respect to different gluten parameters (gluten volume, gluten character, water-binding ability in wet gluten) at respective kneading times.

6 Claims, 3 Drawing Sheets

METHOD AND ARRANGEMENT FOR DETERMINING THE ABILITY OF WHEATFLOUR TO BIND WATER

The present invention relates to a method of determining the optimal ability of wheat meal to bind water in accordance with the preamble of claim 1, and also to apparatus for carrying out the method.

The absorption of water by wheat flour is an important factor when preparing dough for all types of baked products. Normally, a high water absorbency is desirable, since this tends to increase what the product has to offer and therewith optimize the size of the end product, usually bread. However, when baking bread it is also important to produce a product of desired shape and volume.

It is extremely difficult to determine what shape and volume the baked bread will have, solely by taking the consistency of the dough into account. The amount of water that can be bound in wheat flour when preparing dough may vary radically from one sort of wheat flour to another. Different types of wheat flour, as the designation used in this Application, designates wheat flour obtained when producing the flour from wheat that possesses different properties due to genetic conditions, growth conditions (degree of fertilization, wet or dry, warm or cold, dark or light, during the growth period). Different grinding processes can also influence the properties of the flour.

The water absorbed by the wheat flour when preparing dough can constitute a weight factor when baking, when the flour absorbs a large quantity of water. This will result in the bread failing to obtain the optimal shape and volume desired. The flour may also absorb too little water. This will also result in a baking result which is not optimal. It is therefore important to have knowledge of the ability of the wheat flour used to form wet gluten while at the same time noting the character of nature of the wet gluten that constitutes the optimal ability of this particular flour to bind water. Since both the volume of wet gluten and the nature of the gluten changes with different dough preparation times (actually in accordance with the different quantities of kinetic energy applied, which is also dependent on kneading rate), it is necessary to register the kneading time in respect of each such value. Thus, each wheat flour sort will have the optimal water absorption capacity when the wet gluten index of the flour concerned is the highest possible at the same time as the nature of the wet gluten is such as to enable the dough to be handled. The water-binding capacity, or ability, is defined as the difference between wet gluten and dry gluten.

A number of apparatus by means of which the baking properties of wheat can be predicted are available commercially. One apparatus, GLUTOMATIC, marketed by PERTEN INSTRUMENTS, is used to enable the wet gluten volume and the gluten character values, so-called Gluten-index, to be determined by a flour sort. It takes about 15 minutes to make this assessment. The process includes a standard dough working time of 20 seconds. The dough is washed for about 5 minutes to obtain the gluten, whereafter the gluten is centrifuged in order to determine the gluten index. The system also includes apparatus for drying the wet gluten pieces obtained in the centrifuging process, said pieces being dried for a period of 4 minutes so as to obtain a dry gluten index and therewith calculate the gluten water-binding index. Weighing, registering of results, sample handling, take about a further minute with each analysis.

Other apparatus for determining the ability of wheat flour to absorb water are also available commercially. One such apparatus is the FARINOGRAPH which operates on the basis of a given dough consistency value and determines how much water shall be added to the flour in order to obtain this value. In this case, attention is paid to the optimal water-binding capacity of the flour in the gluten part. There is obtained a combined value of water uptake in both the gluten and starch and also in other flour components. The apparatus EXTENSOGRAPH determines the resistance capacity of the dough. The apparatus ALVEOGRAPH determines a similar dough characteristic. The latter three apparatus are thus based on dough analyses, in which both gluten and the starch components or fractions are assessed together. These apparatus are expensive and require trained personnel to carry out the analysis and to evaluate the results from the curves obtained. When determining water-absorption capacity in these apparatus, it is necessary to use sieved flour, whereas when using the GLUTOMATIC apparatus, it is possible to make such assessments on wheat scrap, i.e. on whole wheat kernels.

The main object of the invention is to provide a method which will enable the optimal water absorption capacity of a relevant wheat flour sort to be determined and expressed in terms of a specific kneading time which will provide the greatest possible water-binding capacity in dough-handling processes.

Another object of the invention is to provide a method for determining an appropriate addition of water and/or an appropriate dough working time with which the same baking result for a relevant bread sort can be obtained irrespective of the sort of wheat flour used.

Another object of the invention is to enable characteristic parameters in the form of wet gluten index, gluten character index and the water-binding capacity of gluten at given kneading times to be defined on the basis of a given bread recipe, and therewith be able to look for these properties in wheat fractions that are offered.

A further object of the invention is to provide apparatus for determining an optimal water-absorption capacity of a relevant sort of wheat flour.

The aforesaid objects are achieved with a method having the characteristic features set forth in claim 1. Further properties and further developments are defined in the remaining claims, together with apparatus for carrying out the method.

The invention will now be described in more detail with reference to the accompanying drawings, in which FIG. 1 illustrates a number of curves in which water-binding capacity is defined as a function of the time taken to prepare a plurality of different sorts of wheat flour;

Figure 1:
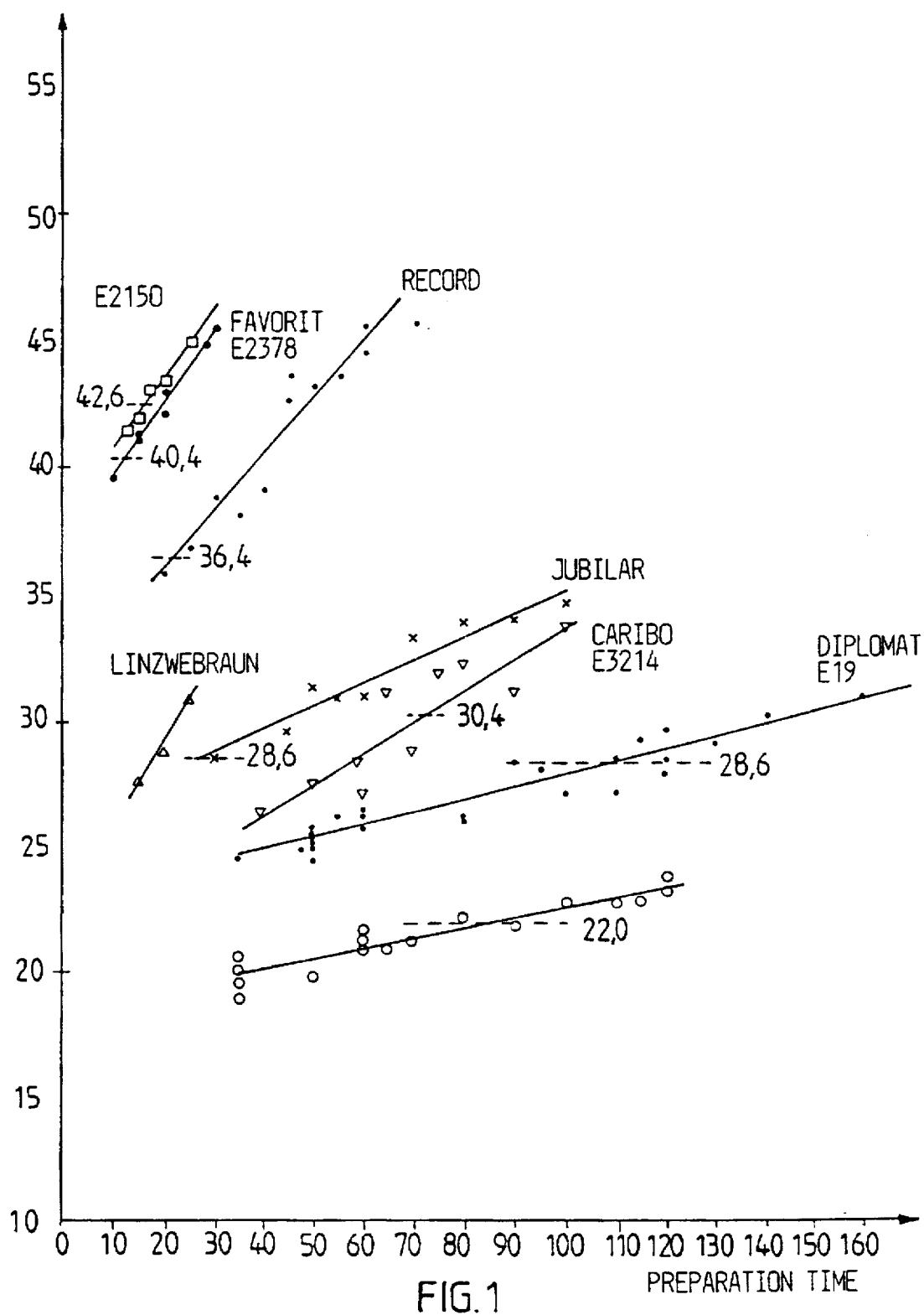

The extent to which a wheat flour will absorb water is dependent on several factors. The first and most significant of these factors is the protein content. The protein complex in a wheat flour has the ability to form gluten, which is a viscoelastic substance, when wheat flour and water are mixed to form a dough. Gluten is referred to as that part of the dough that remains when the dough is washed under running water. Gluten contains the protein substances in the wheat (the main constituents glutenin and gliadin) and the water bound therein. Wet gluten may have different natures (expressed in a strong, average, weak Gluten-index).

The second main component of wheat flour significant to the total amount of water bound in the dough is starch. The wheat grain contains about 65–70% starch. The extent to which water is absorbed by whole, i.e. undamaged, starch corresponds to about 35% of the weight of the starch at normal dough or batter temperatures. When the starch is damaged to a great extent, as can happen when milling the grain, the damaged starch will absorb quantities of water greater than those corresponding to 35%.

Other wheat components, such as pentosanes, dextrins, cellulose, have only a slight influence on water absorption, since they are present in only small quantities. It is true that pentosanes are able to bind water in amounts corresponding to several times their own weight, but wheat flour contains only minor quantities of pentosanes.

The amount of water that is taken-up by a dough in addition to being taken-up by the gluten will depend on the starch and when the starch is damaged will also depend on the extent of this damage.

There is a difference between the water that is bound in the wet gluten and the water that is taken-up by the starch. The amount of water taken to bind the gluten is dependent on the time that the dough is kneaded and the kneading rate, i.e. on how much motive energy is delivered to the protein substances when preparing the dough. The amount of water taken-up by the starch is independent of the motive energy applied.

The consistency of dough is influenced by the amount of water that is taken-up by both gluten and starch. Since both of these amounts may be different with different sorts of wheat flour, it is impossible to determine the appearance and shape of the finished bread solely by assessing the consistency of the dough. The water bond in the gluten fraction and the amount of water taken-up in the starch respectively have different adherences, since the water together with the starch can be dissolved by adding more water during the kneading process.

Thus, the properties of the dough are significant factors in the production of bread when carrying out the process, i.e. in conjunction with kneading, fermentation, etc., and also the appearance of the final product (the bread) after being baked in an oven (form, volume).

Since, as before mentioned, different sorts of wheat have different properties, depending on genetic properties, differences in growth conditions, etc., it is of interest to determine the prerequisites for the production of bread from each wheat delivery.

It is known to determine the amount of wet gluten obtained and the properties of the gluten in terms of strong or weak values (Gluten-index) at a given kneading time, 20 seconds. The present invention enables the optimal water-binding ability of the wheat delivery to be determined. The optimal water-binding ability is defined as the largest amount of water that can be bound by the gluten while maintaining a readily-handled gluten and therewith retaining the nature of the dough.

The apparatus designated GLUTOMATIC and marketed by Perten Instruments mentioned in the introduction will produce a dough from 10 g wheat flour mixed with 4.8 ml water, whereafter the dough is washed to obtain gluten.

The apparatus GLUTOMATIC is used with a standard dough kneading time of 20 seconds, so as to enable a comparison to be made between the wet gluten quantities obtained with different wheat sorts. After being centrifuged in a special centrifuge, the properties of wet gluten are determined in terms of weak or strong properties (Gluten-index) at one and the same dough kneading time, 20 seconds. The apparatus operates at a constant kneading speed.

Since gluten is the functional part in the dough produced from wheat flour in order to obtain bread of optimal volume, and the starch fraction of the dough has a secondary significance in this regard, the measured ability of wet gluten to bind water can constitute an interesting measurement of the optimal wheat flour preparation time.

According to the present invention, the effect of kneading dough at different kinetic or motive energies is investigated, this preferably being effected by keeping the kneading speed constant, and investigating different dough kneading times in order to obtain a curve or graph that is representative of the effect of the preparation time on the ability of the gluten to take-up water with regard to the wheat sort examined, so as to find from said curve an optimum at which the water-binding ability is the highest possible while maintaining a manageable gluten nature of the dough.

FIG. 1 shows a number of curves obtained when testing the effect of different preparation times in obtaining a quantity of wet gluten from a number of different wheat flour sorts with the aid of the apparatus GLUTOMATIC and peripheral equipment. The washing time was kept constant for all tests.

The extent to which water was present was determined by eliminating all water in the wet gluten pieces, by drying the pieces between two heated Teflon plates for 4 minutes. This resulted in a water-binding value for the flour tested, and enabled a mutual comparison to be made between the values of the different flour sorts. As will be seen, the inclination of the curves obtained varies. On the other hand, the curves are straight lines between the values obtained.

As a result, only a few different preparation times need be tested, ideally only two tests, in order to establish the water-binding ability of the gluten obtained with a given wheat flour sort.

Figure 2:
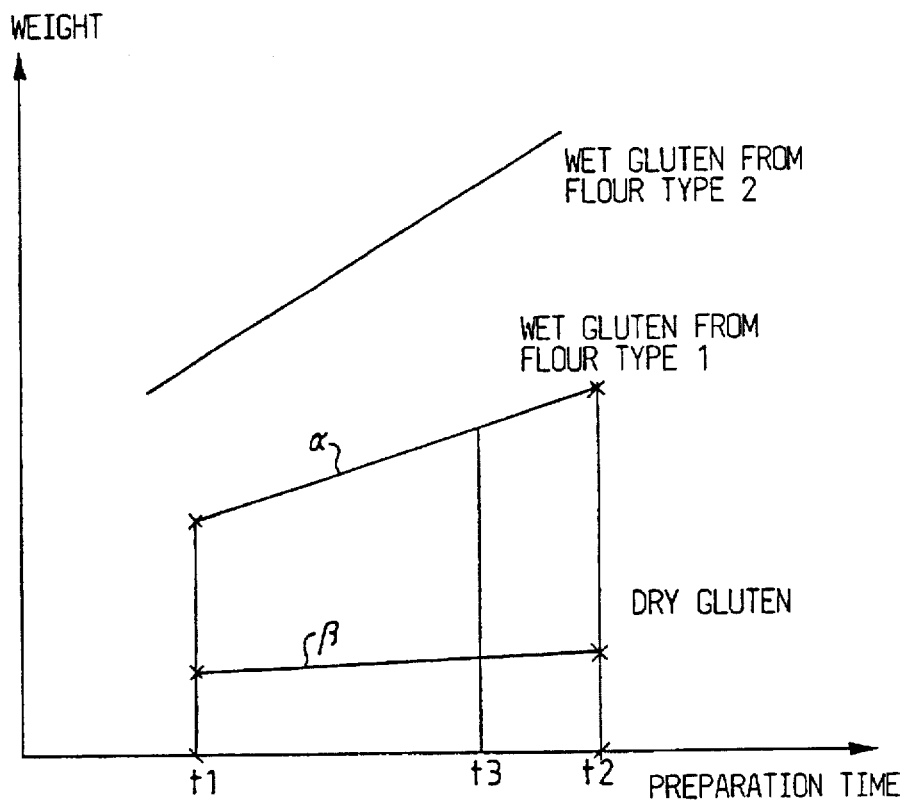
FIG. 2 illustrates the weight of gluten obtained from washed dough as a function of the preparation time with two different sorts of wheat flour.

Two curves can then be drawn-up, as shown in FIG. 2. A first curve is representative of the wet gluten and a second curve or graph is representative of the dry gluten, i.e. representative of the values obtained in respect of the dried wet gluten pieces. If it is assumed that the preparation times for the samples taken were t1 and t2, it is easy to determine the water absorption ability for each time t3 therebetween. The water-binding ability is evident from the span between the two curves obtained. A relevant working time employed in the production of a particular sort of bread has a specific correlation to the preparation time employed with the samples in the given apparatus. It would also seem that the amount of water that must be added to a given amount of wheat flour in order to obtain an optimal baking result is also correlational to the span between the different curves in FIG. 2 for the calculated preparation time.

It is possible to calculate the level of energy that shall be delivered per unit of weight of flour when preparing dough in the GLUTOMATIC procedure, this level of energy being correlational to the kneading time at a given operating speed that shall be applied in an industrial baking process.

The amount of energy delivered can be calculated by multiplying the speed at which the GLUTOMATIC apparatus operates by the length or duration of the dough mixing time when set in relationship with the amount of flour used.

The ability of determining the optimal baking capacity of wheat flour is restricted by the fact that the gluten becomes too strong or too weak to manage preparation of the dough. The optimal water-binding ability of each sort of wheat flour can be defined by the nature or character of the gluten which is satisfactorily strong after a given kneading time and binds as much water as possible in the gluten. It can be mentioned by way of example that in the case of Western baking cultures, an optimal water-binding ability is normally achieved with a Gluten-index of about 60.

Figure 3:
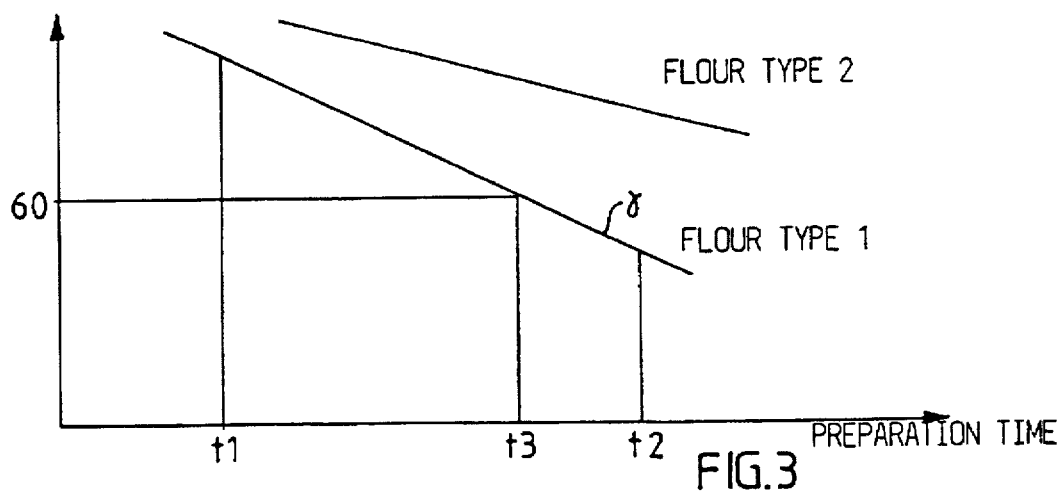
FIG. 3 illustrates the Gluten-index values as a function of the preparation time for an investigated wheat source.

FIG. 3 shows different Gluten-indexes obtained with different working times for one investigated sort of wheat flour. This curve also tends to be straight in the centre of the coordinate system. For instance, if a particular sort of bread requires a Gluten-index value of 60, it will be seen that a preparation time t3 will result in this value.

The preparation time for an actual dough is specifically correlated with the sample preparation time. The correlation for a specific sort of bread can be obtained by test-baking. The amount of water that shall be added to a dough in order to obtain this Gluten-index is determined by examining the weight difference between the wet gluten curve and the dry gluten curve in FIG. 2 at time point t3. The amount of water that should be added is correlational with this weight difference. The correlation for a specific sort of bread which, after all, may include other ingredients than solely wheat flour, can be obtained by test-baking. Once having obtained the correlation for one sort of bread, it is no longer necessary to test-bake, since the inventive method will show the amount of water required.

Figure 4:
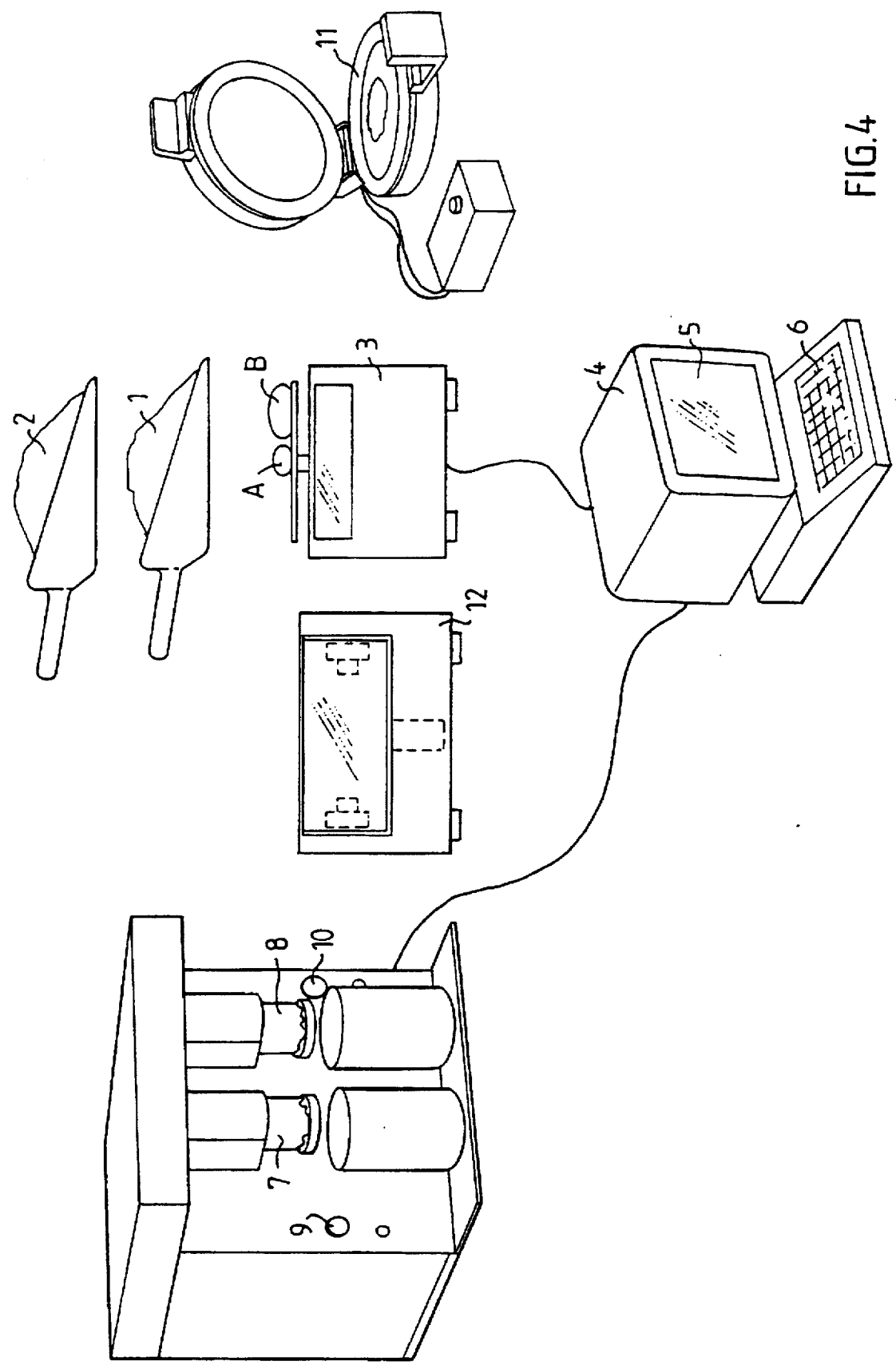
FIG. 4 is a schematic illustration of apparatus for carrying out the inventive method.

FIG. 4 illustrates an arrangement of apparatus by means of which the amount of water to be added and the working time required with regard to an investigated sort of wheat flour in order to bake a particular sort of bread can be obtained.

According to the invention, at least two investigations are carried out with the aid of apparatus in order to arrive at the gluten character values. In the case of the embodiment illustrated in FIG. 4, two investigations are carried out. In this respect, two predetermined, equal quantities of wheat flour 1, 2 to be tested are weighed on scales 3. The scales are connected to a calculating unit, in this case to a computer 4, into which the weighing result is entered by the operator through the medium of keys on a keyboard 6, and stored in said unit. The computer 4 is provided with software which upon completion of a full test program calculates the preparation time and optionally also the amount of water to be added to the tested flour sort in order to obtain a desired sort of bread, and presents the results of these calculations on a screen 5.

Each quantity of flour 1, 2 is mixed with an adapted quantity of water (e.g. 4.8 ml) and then kneaded. The one flour quantity is kneaded for 20 seconds for instance, and the other flour quantity for a period of 60 seconds, for instance. The dough is then washed to remove the starch, leaving a so-called gluten piece. This is done in a respective preparation unit 7 and 8 in a preparation machine which has two such units. A machine of this kind is sold commercially under the trade name GLUTOMATIC 2200, although with this machine the preparation time is the same in both units.

According to the present invention, each unit 7, 8 is equipped with an individual timer means 9, 10 with which the individual working times of the two units 7, 8 can be set. The preparation machine may also be connected directly to the computer 4, so that the of the set working times can be entered into the computer. Alternatively, the operator can insert the set preparation times into the computer through the computer keyboard.

The gluten piece obtained from the preparation units 7, 8 is centrifuged in a known manner in a centrifuge 12 placed in a separate centrifuge cassette having a separate sieve or screen for subsequent separate weighing of one part A of the wet gluten piece obtained subsequent to centrifugation and passing through the filter, and the whole of the wet gluten piece A+B. The Gluten-index value G is obtained by the following calculation:

$$G=100*B/A+B$$

The curve $\gamma$ in FIG. 3 is obtained by carrying out a separate Gluten-index calculation for the two calculations carried out by the computer 4, into which all weighing results are loaded.

The curve $\alpha$ in FIG. 2 is obtained by weighing the whole of the wet gluten piece A+B obtained with each of the two preparations, wherein the time t1 in the illustrated embodiment is 20 seconds and the time t2 is 60 seconds. The curve $\beta$ in FIG. 2 is obtained by drying the wet gluten piece A+B obtained from each preparation in a drier 11, so as to obtain a dry gluten biscuit. This biscuit is then weighed on the scales 3. The computer is also able to calculate the starch content of the tested flour, by making a comparison between the weight of the dry gluten biscuit and the weight of the flour that was initially weighed.

It will be noted that the temperature of the flour and water shall be the same during the whole of the test for all determinations, and thus specific during the actual dough preparing process. The milling processes as used to produce flour from wheat kernels must also be identical in order to enable a true comparison to be made between the results.

In some cases it is only desired to determine the optimal water-absorption capacity of a specific wheat sort. In this case, the computer will only calculate the difference in weight between the wet gluten and the dry gluten, with the aid of the calculated curves $\alpha$ and $\beta$ shown in FIG. 2. One such case may, for instance, be to class wheat according to baking properties immediately after the wheat is harvested. In this case, it may be possible to refrain from determining the Gluten-index, at least with regard to the wet gluten piece obtained from one of the preparation units.

In other instances it may be desired to determine baking properties with regard to a specific Gluten-index value. In this case, the computer will first calculate the curve $\gamma$ in FIG. 3 and then calculate the time t3 which will give the desired specific value. The difference in weight between the wet gluten piece and the dry gluten piece is then calculated at the calculated time point t3.

It is sometimes necessary for one to know which Gluten-index value can be expected with a specific dough kneading time, with knowledge of the water-absorption capacity of the flour gluten content at this time.

In other cases it may be desirable for a bakery to know the preparation time and the amount of water that shall be added to a dough in order to achieve with a sort of wheat flour that is unknown to the bakery the same baking result as that obtained with another well-known sort of wheat flour.

By test-baking different sorts of bread using different bread recipes, the correlations between the values obtained with test preparations and the actual preparation of dough for baking purposes adequate for these bread sorts have been obtained and are found stored in the computer 4. When calculating the correlation value for estimating the amount of water to be added, one factor in this regard may be a comparison between the weight of the dry gluten piece and the weight of the flour being tested. The difference between these two weights denotes the weight of the starch fraction that is washed out of the flour. The formula for obtaining correlation values by test-baking different sorts of flour is also obtained in this case. This formula is stored in the computer 4 and is used by appropriate software in calculating the given properties of a relevant flour sort.

The creation of software of the aforesaid kind is a simple and obvious matter for one of normal skill in this art and will not therefore be described in detail. The computer 4 may be any standard type of computer, for instance a conventional personal computer.

The testing operator need only enter into the computer the sort of bread that is to be baked from the unknown sort of wheat flour. The flour is tested in the aforedescribed manner. The computer then calculates an adequate preparation time and possibly also the amount of water that shall be added, and presents the result(s) on the screen 5.

Other cases are conceivable in which the obtainable values are used to calculate appropriate dough preparation times and water-absorption capacities.

It will be understood that many modifications are possible within the scope of the invention as defined in the following claims. For instance, the test doughs can be prepared one after the other in preparation apparatus that includes only one preparation unit. Furthermore, more than two test doughs may be prepared, for instance test doughs having dough preparation times of 20 seconds, 40 seconds and 60 seconds respectively. However, all preparations must have mutually the same temperature, in order for a comparable result to be achieved.

I claim:

1. A method of determining the optimal water-binding ability of wheat flour to provide bread with a desired baking result, wherein the method comprises a treatment cycle in which a predetermined quantity of wheat flour is mixed with water and prepared by working the flour and water together;

the starch content of the flour is washed out to obtain the gluten content, such as to obtain a wet gluten piece; characterized by repeating the treatment cycle at least twice at mutually different kinetic or motive energies and at mutually equal temperatures;

wherein each wet gluten piece obtained at each preparation time is first weighed with its water content and then dried and re-weighed;

marking the measured weights in a coordinate system for weight in relation to preparation means and joining together the markings in the coordinate system for the weights of the wet gluten pieces so as to form a first curve, and joining the markings for the weights of the dried wet gluten pieces together to form a second curve, wherein the water-binding ability of the gluten for wheat flour at a relevant level of applied energy can be indicated by reading-off the two curves;

determining the character or nature of the gluten at respective applied kinetic or motive energies and connecting these values to form a third curve; and determining on the basis of the resultant readings and determinations of the optimal water-binding ability and therewith the correct water addition and applied kinetic or motive energy to obtain a desired baking result on the basis of the result obtained from test-baking processes with corresponding treatment cycles as the test determinations.

2. A method according to claim 1, characterized in that a first correlation factor between applied kinetic or motive energy obtained when test-determining with a predetermined quantity of flour and virtual addition of kinetic or motive energy for a specific sort of bread is obtained by test-baking.

3. A method according to claim 1, characterized in that a second correlation factor between indicated water-binding ability of the gluten at a specific applied kinetic or motive energy which has been obtained by test-determining with a predetermined quantity of flour and the amount of water that shall be added to a dough for baking bread so as to obtain a desired baking result is determined by test-baking.

4. A method according to claim 3, characterized in that the second correlation factor has a part which is dependent on the difference between the weight of the dry gluten piece and the initial weight of the flour prior to test determination.

5. Apparatus for test-determining with one treatment cycle the optimal water-binding capacity of wheat flour to provide correct water addition and applied kinetic or motive energy to obtain bread having a shape and volume that can be well-determined, comprising:

a sample preparing device (7, 8) in which a predetermined quantity of wheat flour and water are mixed by working the flour and water together while applying a given level of kinetic or motive energy, and in which the starch content of the flour is washed therefrom to obtain its gluten content and therewith a wet gluten piece (A+B), and wherein the apparatus further includes scales (3) for weighing the wet gluten piece and also the dry gluten piece that is obtained by drying the wet gluten piece; characterized in that said sample preparing device (7, 8) is adapted to prepare and weight samples at least two mutually different applied kinetic or motive energies; in that the apparatus further includes:

a calculating unit (4), such as a computer, having storing features and adapted to be fed with and store said different applied kinetic or motive energies used by said sample preparing device (7, 8) and the results from the scales (3) of weighting said wet gluten and dry gluten pieces of said samples prepared in the sample preparing device (7, 8), and to calculate the difference between the respective weights of the wet gluten piece and the dry gluten piece with each sample and to calculate a curve from which the water-binding ability of the gluten is calculatable for the wheat flour concerned at a relevant applied kinetic or motive energy, said calculating unit (4) being provided with stored correlation values and/or correlation formulae for conversion between the energies applied by said sample preparing device (7, 8) to said samples and the values used in the sample preparation processes to applied energies and values adequate for preparing a dough from which bread can be baked, and provided with dedicated software which is effective in calculating preparation time and the amount of water that need be added to a relevant flour in order to obtain a desired baking result, on the basis of the respective values of test-weighing results, test preparation data and stored and/or calculated correlation values fed into the calculating unit (4), and presenting the calculated preparation data needed for an operator providing bread.

6. Apparatus according to claim 5, characterized in that the the sample preparation device (7, 8) and scales (3) in a way known per see are used to obtain a gluten character value of the wet gluten piece (A+B) obtained with each of the at least two samples, and the at least two gluten character values are entered into the calculating unit (4), which, on the basis of said values obtained from the samples, calculates a curve for the gluten character values in relation to the dough-kneading values.

* * * * *